(12) United States Patent
Meredith et al.

(10) Patent No.: US 6,379,967 B1
(45) Date of Patent: Apr. 30, 2002

(54) HERPESVIRUS SAIMIRI AS VIRAL VECTOR

(75) Inventors: David Mark Meredith; Alexander Fred Markham, both of Leeds (GB)

(73) Assignee: The University of Leeds, Leeds (GB)

( * ) Notice: Subject to any disclaimer, the term of this patent is extended or adjusted under 35 U.S.C. 154(b) by 0 days.

(21) Appl. No.: 09/254,326

(22) PCT Filed: Sep. 4, 1997

(86) PCT No.: PCT/GB97/02371

§ 371 Date: Mar. 4, 1999

§ 102(e) Date: Mar. 4, 1999

(87) PCT Pub. No.: WO98/10083

PCT Pub. Date: Mar. 12, 1998

(30) Foreign Application Priority Data

Sep. 4, 1996 (GB) .............................................. 9618477

(51) Int. Cl.⁷ ...................... C12N 15/869; C12N 15/63; C12N 7/00; C12N 7/01; C12N 15/09

(52) U.S. Cl. ................. 435/456; 435/235.1; 435/320.1; 435/325; 435/455; 435/69.1

(58) Field of Search ........................... 435/320.1, 235.1, 435/69.1, 325, 455, 456

(56) References Cited

U.S. PATENT DOCUMENTS 5,424,197 A * 6/1995 Grassmann et al. ....... 435/69.1
5,672,344 A * 9/1997 Kelley et al. .............. 424/93.2

* cited by examiner

*Primary Examiner*—David Guzo
*Assistant Examiner*—Gerald G. Leffers, Jr.
(74) *Attorney, Agent, or Firm*—Myers Bigel Sibley & Sajovec

(57) ABSTRACT

The invention relates to herpesvirus saimiri viruses that are genetically modified by mutations and/or deleting specific essential and non-essential genes. The essential genes are required in replication of viral genes and are needed for viral proliferation. The non-essential genes can represent sites for the insertion of heterologous genetic material.

32 Claims, No Drawings

SEQUENCE LISTING

```
<160> NUMBER OF SEQ ID NOS: 16

<210> SEQ ID NO 1
<211> LENGTH: 18
<212> TYPE: DNA
<213> ORGANISM: Herpesvirus saimiri

<400> SEQUENCE: 1
tgaattcgga tccgcatg                                                 18

<210> SEQ ID NO 2
<211> LENGTH: 18
<212> TYPE: DNA
<213> ORGANISM: Herpesvirus saimiri

<400> SEQUENCE: 2
cgcgacttaa gcctaggc                                                 18

<210> SEQ ID NO 3
<211> LENGTH: 34
<212> TYPE: DNA
<213> ORGANISM: Herpesvirus saimiri

<400> SEQUENCE: 3
aacgaattcg gatccttaat aataatgagc tgta                               34

<210> SEQ ID NO 4
<211> LENGTH: 34
<212> TYPE: DNA
<213> ORGANISM: Herpesvirus saimiri
```

<400> SEQUENCE: 4
ttgcttaagc ctaggaatta ttattactcg acat                          34

<210> SEQ ID NO 5
<211> LENGTH: 32
<212> TYPE: DNA
<213> ORGANISM: Herpesvirus saimiri

<400> SEQUENCE: 5
ggcgaattcg tctataactg actgggttgc tg                            32

<210> SEQ ID NO 6
<211> LENGTH: 34
<212> TYPE: DNA
<213> ORGANISM: Herpesvirus saimiri

<400> SEQUENCE: 6
aattcatggc aacgaagaca gcgcaaccta gcgc                          34

<210> SEQ ID NO 7
<211> LENGTH: 26
<212> TYPE: DNA
<213> ORGANISM: Herpesvirus saimiri

<400> SEQUENCE: 7
gtaccgttgc ttctgtcgcg ttggat                                   26

<210> SEQ ID NO 8
<211> LENGTH: 32
<212> TYPE: DNA
<213> ORGANISM: Herpesvirus saimiri

<400> SEQUENCE: 8
gccctgcagg cagttactca ccatagcttg ag                            32

<210> SEQ ID NO 9
<211> LENGTH: 33
<212> TYPE: DNA
<213> ORGANISM: Herpesvirus saimiri

<400> SEQUENCE: 9
gccctgcagc aagtgtccaa gctctacttg tgc                           33

<210> SEQ ID NO 10
<211> LENGTH: 34
<212> TYPE: DNA
<213> ORGANISM: Herpesvirus saimiri

<400> SEQUENCE: 10
ggggcatccc tattgatgtg ccaagcaata gggt                          34

<210> SEQ ID NO 11
<211> LENGTH: 33
<212> TYPE: DNA
<213> ORGANISM: Herpesvirus saimiri

<400> SEQUENCE: 11
cgcggtaccc acatgtctat aatcgactgg gtt                           33

<210> SEQ ID NO 12
<211> LENGTH: 33
<212> TYPE: DNA

```
<213> ORGANISM: Herpesvirus saimiri

<400> SEQUENCE: 12
cggggtaccc tgagtcatta gtagtagctc atg                              33

<210> SEQ ID NO 13
<211> LENGTH: 31
<212> TYPE: DNA
<213> ORGANISM: Herpesvirus saimiri

<400> SEQUENCE: 13
gccgaatccc acagtgccaa gcttgccagt t                                31

<210> SEQ ID NO 14
<211> LENGTH: 32
<212> TYPE: DNA
<213> ORGANISM: Herpesvirus saimiri

<400> SEQUENCE: 14
cgcctgcagg gtgtataact gagtgttaca gc                               32

<210> SEQ ID NO 15
<211> LENGTH: 31
<212> TYPE: DNA
<213> ORGANISM: Herpesvirus saimiri

<400> SEQUENCE: 15
gggctgcagg ctgtacactc agttatacac c                                31

<210> SEQ ID NO 16
<211> LENGTH: 30
<212> TYPE: DNA
<213> ORGANISM: Herpesvirus saimiri

<400> SEQUENCE: 16
cccgcatgca cttgatccag gacatgcttc                                  30
```

HERPESVIRUS SAIMIRI AS VIRAL VECTOR

The invention relates to a method of virus manipulation; means therefor and products thereof which have particular, but not exclusive, application in gene therapy.

Gene therapy of many diseases is now theoretically possible, as a result of recent advances in human genetics. The primary goal is the conversion of cell phenotype from a diseased to a normal state, through the delivery of trans-dominant acting genetic material. The conversion of this technology from cell culture systems to in vivo experimental models (and subsequently to the clinic) requires the development of new methods for efficient gene delivery in a controllable manner. It is becoming evident that whilst human genetics is moving at a rapid rate in the identification of disease-specific mutations, there is a relative lack of gene delivery system development. At present, there is a choice of either liposome, DNA aggregate or virus-based systems.

Liposome delivery is still very inefficient in DNA transfer (1), DNA aggregates formed between virus particles and charged materials such as polylysine do enhance DNA uptake (2) but standardisation of preparations is very difficult. Retrovirus and adenovirus vectors both have constraints in the size of heterologous DNA incorporated in the vector (3,4) and are unreliable in achieving long-term heterologous gene expression. Retroviruses integrate into the host genome but are difficult to produce as high titre stocks and have an inherently high rate of mutation through errors introduced during reverse transcription. Despite their broad cell tropism, adenoviruses induce a cell-mediated immune response and the nucleic acid is not stable long-term in infected cells (5).

Herpesviruses represent promising candidates for development as vectors, in part due to their ability to maintain their genome in cells in an episomal form which is blocked from replication. Their capacity for packaging heterologous DNA sequences is potentially >50 Kbp (6) and most are easy to manipulate in vitro. Herpes simplex derived vectors are likely to have some of the same problems as adenoviruses, in that the majority of the population already have a well-developed immune response to the virus. Other non-human herpesviruses which are capable of infecting human cells, however, should not suffer this disadvantage.

Herpesvirus saimiri (HVS) is a lymphotropic rhadinovirus ($_{\gamma}2$ herpesvirus) of squirrel monkeys (*Saimiri sciureus*). The virus may be routinely isolated from peripheral lymphocytes of healthy monkeys and causes no apparent disease in the species. The virus genome may be detected in an episomal form in T cells and genome transcription appears limited to three genes in the non-lytic ("latent") state. The complete virus genome has been sequenced and shares many features in common with the human Epstein-Barr virus (EBV). The genetic organisation consists of a single unique coding region of DNA, 112.930 bp in length, flanked by a variable number of non-coding repeat sequences. There are 76 open reading frames, 60 of which have similarities with genes found in other herpesviruses (7). The remaining genes share sequence homology (at the level of protein) with human genes of known function, including complement control proteins, cell surface antigen CD59, cyclin D and G protein-coupled receptors (8, 9).

The virus has been divided into three distinct strains termed A, B and C based on their inability (A and B) or ability (C) to be oncogenic in certain other monkey species. C strains have the ability to transform human T cells to limited independent growth in vitro (10). This ability to transform cells is due to a gene termed STP (11) which has marked variability in protein sequence between strains such that only STP from C strains is able to transform cells (12). STP is not important for the normal lytic cycle of the virus or episomal maintenance and natural deletion mutants for this region of the virus genome exist (13); these strains are not oncogenic. Virus strains which lack this gene have been constructed which express selectable drug resistant markers (14). These viruses have been used to demonstrate that they are capable of infecting a wide range of human cell types, transferring heterologous genes with high efficiency and maintaining long-term expression in the absence of selective pressure. There is no evidence that this virus is able to produce any disease in man, although it is capable of infecting human cells. Thus it is likely that this virus represents a good starting point for the development of a non-replicating, safe vector for human cells. There is however a lack of basic understanding of how HVS replicates, particularly regarding transcriptional control and DNA replication.

Of all herpesviruses sequenced so far, HVS has the most homology with EBV. However the coding region is significantly smaller. Distinct gene blocks appear to be closely related between these two viruses, and indeed the herpesviruses in general. HVS differs from other herpesviruses due to the presence of certain genes which have not been identified in any other herpesvirus to date. Every virus vector in human trials to date has been disabled either through the deletion of genes which are non-essential for growth in culture or the deletion of essential genes and their provision in trans from helper cell lines. Extrapolation from the well studied herpesviruses allows us to predict that deletion of certain HVS membrane proteins will prevent cell-cell spread. Furthermore, the inactivation of proteins which control essential transcriptional switches, such as E1A in adenoviruses (17) and IE 175 in herpes simplex (18) will inevitably make such viruses replication incompetent. Thus, a major aim of this application is focussed on the construction of mutant viruses which are unable to activate early and late gene expression. The target genes are the two transcriptional control proteins which are the products of ORF 50 and 57, and likely to be essential for growth in tissue culture.

Published data (14) indicates that Strain 11/S4-derived viral vectors are only capable of limited growth in certain cell lines. Thus the need to delete, block or manipulate transcriptional control protein genes should only be necessary in cell lines that support viral replication. However, it may be desirable, in order to produce a virus for the purpose of gene delivery which one can use confidently, to produce a virus which is either unable to produce or which produces non functional transcriptional control proteins.

It is also another major aim of this application to identify genes which are non-essential for growth and then delete at least a part of at least one of these genes in order to facilitate the insertion of heterologous genetic material into the viral genome.

There currently exists a plasmid designed for recombination with herpesvirus saimiri which plasmid is designed to insert heterologous genetic material into the viral genome at a predetermined location, the location being the junction between the single unique coding region of DNA and a non-coding repeat sequence of herpesvirus DNA. However the plasmid is relatively inflexible in terms of what can be cloned into the viral genome. For example, there are few suitable restrictions sites and therefore the plasmid is not suitable for use commercially. We have therefore aimed in this application to identify non-essential genes for growth with a view to deleting at least a part of at least one of said genes with a view to providing artificial cloning sites for the insertion of large amounts of any selected heterologous genetic material. It will be apparent that the said deletion of non-essential genes and the subsequent insertion of heterologous genetic material will most advantageously be undertaken when large amounts of heterologous genetic material are to be inserted into the viral genome.

We aim in another aspect of our application to provide herpesvirus saimiri which has been manipulated so as to delete at least a part of at least one transcriptional control gene and, ideally, also at least a part of at least one gene that encodes a non-essential growth protein. We favour this aspect because the greater the number of viral genome manipulations the greater the safety of the manipulated virus. In view of this fact we also favour manipulation of the herpesvirus saimiri genome to bring about deletion, partially or wholly, of the STP gene. We favour this latter manipulation even in the instance where Strains A or B are to be utilised because we consider such a manipulation to increase the likely safety of the resultant manipulated virus.

It will be apparent from the above that there is a need to provide a suitable gene delivery system to enable intracellular delivery of genetic material which delivery is undertaken safely and thus without any cytopathological consequences at least on the target cell.

It is therefore a first object of the invention to provide a gene delivery system which is safe and controllable.

Furthermore, in view of the amount of genetic material likely to be delivered it is also an object of the invention to provide a gene delivery system which is adapted to accommodate large amounts of genetic material such as DNA sequences of 4 Kbp and up to 20 Kbp and, ideally, >50 Kbp.

It is a further object of the invention to provide a gene delivery system which allows selective recombination of at least a given gene, or part thereof, into same so as to deliver at least said selected gene, or part thereof, to a target cell.

In its broadest aspect the invention concerns the provision of mutant viruses which are unable to activate early and late gene expression. In other words it concerns the provision of a virus which is unable to replicate in a target cell and more preferably in human cells and/or the provision of mutant viruses which are adapted to accommodate relatively large amounts of heterologous genetic material.

According to a first aspect of the invention there is therefore provided a herpesvirus saimiri which has at least one mutation in a gene involved in virus replication whereby the mutation is such to prevent the virus replicating in a target human cell.

In a preferred embodiment of the invention said gene is either one or both of the transcriptional control protein genes ORF 50 and/or ORF 57.

Preferably further still said mutation comprises partial or complete deletion of one or both of said genes.

In yet a further embodiment of the invention the said herpesvirus saimiri is a strain either lacking or having a mutation in the STP gene so that the virus is unable to transform a target cell and so is unable to produce an oncogenic phenotype.

Preferably said virus is further manipulated so that at least a part of at least one gene encoding a non-essential growth protein is deleted. Ideally said gene is ORF4, ORF14, ORF15, ORF16 or ORF51.

In yet a still further preferred embodiment of the invention said virus is provided with an insertion site into which selected heterologous material can be inserted. Preferably the virus is manipulated so that insertion occurs either within, adjacent, or remote from, a deletion site for the deletion of at least a part of a non-essential growth protein gene; or in or adjacent at least one non-coding repeat sequence and more preferably at the junction between the single unique coding region of DNA and a non-coding repeat sequence. More preferably still, said virus is manipulated so that only one of said non-coding repeat sequences is present at one or both ends of the single unique coding region.

In the instance where insertion occurs within or adjacent said deletion site AND said deletion concerns either partial or whole deletion of one or more of the following genes ORF4, ORF14, ORF15, ORF16 or ORF51.

According to a yet further aspect of the invention there is provided a herpesvirus saimiri which has at least one mutation in at least one gene encoding a non-essential growth protein.

In a preferred embodiment of the invention said gene is either one or more of ORF4, ORF14, ORF15, ORF16 or ORF51.

Preferably further still said mutation comprises partial or complete deletion of one or more of said genes.

In yet a further preferred embodiment of the invention the said herpesvirus saimiri is a strain either lacking or having a mutation in the STP gene such that the virus is unable to transform a target cell and so is unable to produce an oncogenic phenotype.

Preferably said virus is further manipulated so that at least a part of at least one gene involved in virus replication is deleted. Ideally said gene is ORF50 and/or ORF 57.

In yet a further preferred embodiment of the invention said virus is provided with an insertion site into which selected heterologous material can be inserted. Preferably the insertion site is within, adjacent, or remote from, the site of said deletion of one or more of said genes.

According to yet a further aspect of the invention there is provided a herpesvirus saimiri either having therein or adapted to have inserted therein at least one preselected heterologous genetic fragment adjacent a deletion site which deletion site represents a site for partial or whole deletion of at least one gene encoding a non-essential growth protein.

In a preferred embodiment of the invention said virus is also provided with a mutation in a gene involved in viral replication so as to prevent viral replication following insertion of said virus into a target cell.

More preferably said virus is a strain either lacking or having a mutation in the STP gene such that the virus is unable to transform a target cell and so is unable to produce an oncogenic phenotype.

According to a further aspect of the invention there is provided a herpesvirus saimiri either having therein or adapted to have inserted therein at least one preselected heterologous genetic fragment at the junction of the single coding region and a non-coding region and further wherein said has viruses been manipulated so that only a reduced number of non-coding repeat sequences is present at one or both ends of the single coding region and there is also provided a mutation in a gene involved in viral replication so as to prevent viral replication following insertion of said virus into a target cell.

Preferably said number of non-coding repeat sequences is 5 or less and ideally one.

According to a yet further aspect of invention there is provided a transfer vector which enables insertion of a heterologous genetic fragment into herpes saimiri virus DNA.

Preferably said insertion involves any one or more of the afore described methods of insertion. In a preferred embodiment of this aspect of the invention said vector includes a plurality of unique restriction sites and more preferably three unique restriction sites. In addition, said vector includes a beta-galactosidase gene which is preferably under the control of the HCMV IE 3 promoter. More preferably the said vector is derived from pRUNeo (16) and ideally is prupoly.

According to yet a further aspect of the invention there is provided a herpesvirus saimiri which has at least one mutation in a gene involved in virus replication whereby the mutation is such to prevent the virus replicating in a target cell and also at least one mutation in a gene encoding a non-essential growth protein.

In a preferred embodiment of the invention said herpesvirus saimiri also has a mutation in the STP gene.

Preferably said mutations comprise either partial or complete deletion of said genes.

Preferably further still said gene involved in virus replication comprises either one or both of the transcriptional control protein genes ORF50 and/or ORF57: and said gene encoding a non-essential growth protein is one or more of the following genes: ORF4, ORF 14, ORF15, ORF16 or ORF51.

It will be apparent from the above that the preferred virus of the invention comprises a number of advantageous combinations of genetic mutations which combinations serve to disable and enable the virus so as to make it safe and controllable. By the term disable we mean the prevention of viral replication in a target cell and by the term enable we mean the capacity to accommodate the insertion of a relatively large amount of heterologous genetic material. More desirably still, said advantageous combination also provides for a virus unable to transform a target cell and so unable to produce an oncogenic phenotype.

According to a yet further aspect of the invention there is provided a target cell including at least a part of the herpesvirus saimiri gene therapy vector.

According to a yet further aspect of the invention there is provided a cell transformed with a herpesvirus saimiri vector as afore described.

According to a yet further aspect of the invention there is provided a method of delivering selected heterologous genetic material to a target cell comprising exposing at least said target cell to a herpesvirus saimiri which includes at least said preselected heterologous material under conditions which favour infection of said cell with said virus.

An embodiment of the invention will now be described by way of example only with reference to the following materials and methods.

Isolation and Characterisation of Viral Mutants

The manipulated virus is a modified from of strain 11, which does not contain ORF1 (STP gene). Although we would normally have chosen a "wild-type" strain, vectors will inevitably have to be based on a virus which has had this gene removed. The modified strain may have essential genes deleted and therefore Helper Cell Lines may be produced (detailed later). These were established through co-transfection with a suitable HVS genomic clone plus pSV2Neo, and cell clones isolated which are G418 resistant. These cell clones were first screened by PCR for the presence of the appropriate gene sequences and those testing positive were analysed by RT-PCR for the presence of RNA transcripts of the gene provided in trans. Appropriate clones were expanded and used for co-transfection with virus DNA and deletion construct. Viruses which express β-galactosidase (as measured by the metabolism of X-gal) were tested for their ability to replicate in helper cells and normal Vero cells, and subsequently in human cell types of differing lineages. Published data indicates that strain 11-derived vectors are capable of limited growth in certain cell-lines of B cell (Raji) and human foetal fibroblast (HFF) origin. Raji cells (EBV transformed) are not representative of normal human cells, therefore we assessed the growth characteristics of these viruses in lymphoid cells isolated from fresh adult human peripheral blood taken from healthy volunteers and primary human embryo fibroblasts and epithelial cells which are available from commercial sources. Replication was assessed through expression of β-galactosidase (evidence of infection and cell-cell spread), presence of episomal DNA, and expression of "typical" early and late genes detected by RT-PCR. Genome persistence in these cells was assessed through measuring the percentage of cells capable of expressing the reporter gene through several cell generations in conjunction with assaying for the presence of episomal virus DNA (19).

Production of Recombinant Viruses with Deleted Genes

Extracellular, cell-released virus was harvested by centrifugation at 30,000 g for 2 h at 4° C. The semi-purified virus pellet was resuspended in 10 mM Tris/HCl, 1 mM EDTA (TE) pH 8.0. SDS was added to 1% w:v and Proteinase K added at 100 μg/ml. The sample was incubated at 50° C. for 16 hours and then treated with 50:50 (w:v) phenol/chloroform mix (5 extractions). The aqueous phase was removed, adjusted to 0.2M with sodium acetate pH 5.0 and 3 volumes of absolute ethanol added. The DNA precipitate was spooled from the tube, air dried and then redissolved in an appropriate volume of TE buffer. DNA concentration was measured by the absorbance of the sample at 254 nm in a spectrophotometer. Purified virus DNA was cotransfected into OMK (ATCC CRL1556) cells with the respective plasmid construct using DOTAP reagent. After 24 hours the culture medium was removed and replaced with medium containing 2% heat inactivated FCS. The cell monolayers were then observed until the development of an extensive cytopathic effect was apparent. At this stage, cell-released virus was harvested and used to infect new subconfluent monolayers of OMK cells. These were overlaid after 24 hours with a 1% agar overlay in phenol red-free DMEM/2% heat inactivated FCS. After 48 hours, X-gal was added to a final concentration of 100 μg/ml, in order to identify virus plaques which were expressing beta galactosidase. Blue plaques were then picked and were subjected to two further rounds of plaque purification, or until the virus population was homogenous. These viruses were then tested for the correct homologous recombination events using PCR and Southern blotting.

Production of Recombinant Viruses which Contain Heterologous Genes

Purified virus DNA, prepared as described above, was co-transfected into OMK cells with plasmid vectors (pJG101–105 and/or pAW 201, 202, 203, 205, 207 or 209) which contain the appropriate heterologous gene replacing the beta-galactosidase sequence for recombination into either non-essential or essential genes, or intergenic regions. Recombinant virus which no longer expresses beta galactosidase was selected and plaque purified in the same manner as that described in the previous section.

Infection of Cells in vitro with HVS

High titre virus stocks were produced by low multiplicity of infection of either OMK or Vero cells. Cell-released virus was titrated in either OMK or Vero cells and stored at −70° C. The amount of virus required to infect any specific cell type at 100% efficiency was assessed by infection of a defined number of cells at various multiplicities of infection with a beta-galactosidase expressing virus. Adherent cells were infected by the addition of virus in a minimum volume of culture medium and incubated at 37° C. for 2 hours with gentle agitation. This medium was then removed and replaced with an appropriate quantity of fresh medium. Non-adherent cells were harvested, counted and between $10^6$ and $10^7$ cells resuspended per 1 ml of virus at an appropriate concentration to achieve 100% infection efficiency. After 2 hours incubation with gentle agitation the cells were treated in the same manner as described for adherent cells.

Production of Helper Cell Lines

The virus genes which were to be expressed in a stable cell line, in trans, were cloned in a suitable plasmid vector under control of their own, or heterologous 5', and 3', control sequences. This plasmid may also contain a selectable marker, eg the neomycin phosphotransferase gene which confers resistance of eukaryotic cells to the drug G418. Alternatively this gene may be provided on a separate plasmid, again under the control of heterologous eukaryotic control sequences, for instance the SV40 early promoter and elppropriate polyadenylation signals. In all cases, cell lines were established thus. $5 \times 10^5$ cells (or sufficient to give 40–50% confluence) such as Vero or OMK were plated out onto 10 cm diameter tissue culture dishes in 10 ml of DMEM/10% foetal calf serum and incubated for 12–18 h at 37° C. in an humidified atmosphere containing 5% $CO_2$ in air. After this period 2 µg plasmid was transfected into the cells using DOTAP reagent as described previously for transfection of virus DNA. This may be either a single plasmid which contains the appropriate gene and the selectable marker gene, or a mixture of 2 µg of each plasmid. Cells were then incubated at 37° C. in a humidified atmosphere containing 5% $CO_2$ in air for a further 48 hours. At this stage, the now confluent monolayers were detached from the plastic dish through removal of the medium, washing the 2×10 ml of phosphate buffered saline (PBS, Life Technologies inc, cat no. 20012) and treatment with 2 ml trypsin (0.25% w:v)/EDTA(0.2% w:v) solution in PBS, Fresh medium was then added to the cell suspension, the cells counted and then plated out into 96 well plates for cloning at limiting dilution or dispensed at $10^4$ cells per 10 cm dish. The culture medium (DMEM/10%FCS) was supplemented with an appropriate concentration of G418 which is sufficient to cause 100% kill of non-transfected cells. The concentration is dependent both on cell passage number and cell type. A typical concentration for Vero cells at passage 150 is 800 µg/ml. Cells were then replaced in the previously described growth environment and observed at regular intervals for cell killing. Culture medium was replaced approximately every 3–4 days depending on cell death/growth rate. After 7–14 days individual clones of cells have grown and were then picked, grown to appropriate numbers and tested for the expression of the HVS gene transfected. This can either be achieved through use of either immunofluoresence, Northern Blotting or RT-PCR using methods well known to the art.

Assessing Virus Safety

The ability of the modified virus to replicate was assessed by measurement of virus gene expression using RT-PCR for a selection of immediate-early, early and late genes. Additionally, tissue culture supernatants from transduced cells were incubated with indicator OMK cells, to detect any possible infectious virus release.

3 Insertion Recombination Vector

This strategy produces a recombination vector to allow insertion of heterologous genes at the 3' end of the HVS L DNA. pSJNeo (from R. Grassman) contains 9.4 kb of HVS DNA which contains the H-L DNA junction. A SmaI cleavage site located 35 bp within the first H repeat unit was changed to a SalI site to allow insertion of the neo gene. This vector, however, is a large, low copy vector and is therefore unsuitable for insertion of large heterologous genes. An expression vector, pSA91, was chosen to make the new recombination vector. This vector is produced at high copy number and contains the hCMV IE promoter to drive gene expression. To produce an efficient expression vector that allows recombination, the HVS DNA sequence was excised from pSIneo and inserted into a unique NarI site located 5' to the promoter, using linker adapters. This vector is designated pJG101.

ORF06 Deletion

ORF06 (located between bp 12584 and 15967) encodes the major DNA binding protein, thus deletion of this gene makes the virus replication deficient. To make a recombination cassette for deletion of ORF06 flanking DNA regions were excised from pSS54 which contains the region of HVS DNA from 11507 to 18013 (the KpnIF fragment). The KpnI (11507)-HaeII (12613) 1106 bp fragment 5' to the ORF06 coding region and the SphI (15258)-BglIII (16407) 1149 bp fragment were excised and ligated together via synthetic oligomers. The oligomers also contain EcoRI and BamHI restriction sites, as shown below, to allow insertion of heterologous genes. It is necessary to maintain part of the 3' end of ORF06 as this contains the promoter for ORF07. The ligated KpnI-BglIII fragment was inserted into the pBluescript KS cloning vector to create the recombination cassette pJG102.

Sequence of oligomers to link the fragments

TGAATTCGGATCCGCATG (SEQ ID NO:1)

CGCGACTTAAGCCTAGGC (SEQ ID NO:2)

HaeIII EcoRI BamIII SphI

ORF06 Construction to Generate Helper Cell Line

To produce HVS deleted for the ORF06 coding region, it is necessary to provide the ORF06 gene product in trans. This was achieved by producing a stable helper cell line. The ORF06 gene was excised from pSS54 as a HaeII (12613)-PstI (15998) fragment. Synthetic oligomers (as shown below) were used to precisely create the start of the coding region of ORF06 and to allow insertion into the expression vector pSVK3 (Pharmacia). Following ligation of the synthetic oligomers to the 5' end of the ORF06, the EcoR1-Ps1 fragment was ligated to pSVK3 to create pJG103. This drives expression from the SV40 early promoter, use of an alternative promoter minimises recombination events in the helper cell line.

Oligomer sequences

AATTCATGGCAACGAAGACAGCGCAAC-CTAGCGC GTACCGTTGCTTCTGTCGCGTTG-GAT (SEQ ID NO:6)

EcoR1 ORF06 Start HaeII (SEQ ID NO:7)

ORF51 Deletion ORF51 encodes the potential receptor binding membrane protein of HVS, therefore deletion of this gene renders the virus non-infectious. ORF51 is located between 72626 and 73432 of the HVS genome. To produce ORF51 flanking sequences for the recombination cassette, the BamHI (71692)-HpaI (72602) 910 bp fragment 5' to the ORF51 coding region and the Bst1107I (73395)-PstI(73998) 601 bp fragment 3' to ORF51 were excised from pKK104 which contains the HVS EcoRI D fragment from 63020 to 77574, and ligated together via synthetic oligomers. These oligomers also contain EcoRI and BamHI restriction sites to enable insertion of heterologous genes and in addition the sequence required to maintain the polyA for ORF52. Following ligation the BamHI-PstI fragment was ligated to the cloning vector pSP73 (Promega) to create the recombination cassette pJG104.

Synthetic oligomer sequences

AACGAATTCGGATCCTTAATAATAATGAGCTGTA (SEQ ID NO:3)

TTGCTTAAGCCTAGGAATTATTATTACTCGACAT (SEQ ID NO:4)

HpaI EcoRI BamHI ORF52 polyA Bst1107I

ORF51 Construction to Generate Helper Cell Line

The ORF51 gene was excised from pKK104 as a HpaI (72602)-StuI (73495) 806 bp fragment and cloned into the SV40 expression vector pSVK3. EcoRI linkers were ligated to the 5' and 3' ends of ORF51 to facilitate this cloning reaction. The resulting ORF51 expression vector was designated pJG105.

ORF 57 Deletion Orf 57 encodes a transcription activator with homology to HSV-1 UL54, an essential immediate early gene. To generate a virus containing a complete deletion of ORF 57, regions adjacent to the coding region of ORF57 were amplified to allow homologous recombination with viral DNA. Primers have been designed; 5'-d GGC GAA TTC GTC TAT AAC TGA CTG GGT TGC TG (SEQ ID NO:5), 5'-d GCC CTG CAG GCA GTT ACT CAC CAT AGC TTG AG (SEQ ID NO:8), 5'-d GCC CTG CAG CAA GTG TCC AAG CTC TAC TTG TGC (SEQ ID NO:9), 5'-d GGG GCA TCC CTA TTG ATG TGC CAA GCA ATA GGG T (SEQ ID NO:10), these amplify two regions of HVS respectively; 77850 to 78260 and 79530 to 80120, suitable restriction sites have been incorporated into the primers to assist in cloning. A triple ligation was performed using these fragments and pUC18, previously digested with EcoRI and SphI, to derive pAW101. This plasmid was then linearised using PstI and SalI and ligated with the lacZ gene under the control of the hCMV IE promoter, to generate PdeltaORF57 which has been deposited with the National Collection of Industrial and Marine Bacteria Ltd (NCIMB), 23 St Machan Drive, Aberdeen, AB2 1RY; Deposition Number 40894.

To generate a helper cell line, a fragment containing the coding region of ORF57 was amplified using PCR, and ligated with a T vector, pCRII, to derive pAW103. This was then cloned into the plasmid pBKCMV to generate ORF57 under the control of the HCMV 1E promoter PBKCM-VORF57 which has been depositied with the NCIMB, as above, Deposition Number 40895.

HVS Insertional Inactivation Constructs

Insertional inactivation is a less preferred method of preventing a gene from functioning, as it relies upon the placing of the indicator β-galactosidase gene within the coding sequence of the appropriate gene, without removal of any part of the open reading frame. There is a risk of recombination events occurring which lead to deletion of the β-gal sequence and no ligation of the open reading frame enabling reactivating of the gene.

To generate an insertionally inactivated gene, a transfer vector was constructed which inactivated each respective gene by inserting the lac Z gene under the control of a I.E. CMV promoter into the 5' coding region of the ORF. This inactivated gene wag then inserted into the viral genome by cotransfection of the plasmid and HVS viral DNA to derive a recombinant virus, which will then be plaque purified.

Plasmid Constructions

ORF 4/Complement Control Protein pJC81 -KpnB was digested with BglII and PstI to generate 1152 bp fragment containing the coding region of ORF4. This fragment was ligated to pUC18, to derive pUCORF4. This plasmid was linearised using BglII, blunt ended using T4 DNA polymerase, and ligated with a blunt ended fragment containing the lacZ gene under the control of an IE CMV promoter, to generate pAW201.

ORF 14/Small IE Gene pACYC184-EcoF was digested with EcoRI and PstI to generate 3189 bp fragment containing the coding region of ORF 14. This fragment was ligated to pUC18, to derive pUCORF14. This plasmid was linearised using KpnI, blunt ended using T4 DNA polymerase, and ligated with a blunt ended fragment containing the lacZ gene under the control of an IE CMV promoter, to generate pAW202.

ORF 15/CD59 Homologue pACYC184-EcoF was digested with SstI and PstI to generate 2415 bp fragment containing the coding region of ORF 15. This fragment was ligated to pUC18, to derive pUCORF15. This plasmid was linearised using MunI, blunt ended using T4 DNA polymerase, and ligated with a blunt ended fragment containing the lacZ gene under the control of an IE CMV promoter, to generate pAW203

ORF 50/Major Transcriptional Activator pACYC 1 84-BcoD was digested with BglII and PstI to generate 4149 bp fragment containing the coding region of ORF 50. This fragment was ligated to pUC18, to derive pAW204. This plasmid was digested with Pst1 and ligated with a DNA fragment containing the lacZ gene under the control of an IE CMV promoter, to generate PdeltaORF50 which has been deposited with the NCIMB, as above, Deposition Number 40892. A helper cell line was constructed using PUCPST deposited with the NCIMB, as above, Deposition Number 40893 which is pUC 18 containing a Pst1 fragment of HVS DNA encompassing both exons of the gene.

ORF 57/IE Gene pACYC184-EcoJ was linearised using BglII, blunt ended using T4 DNA polymerase, and ligated with a blunt ended fragment containing the lacZ gene under the control of an IE CMV promoter, to generate pAW206.

In order to construct a helper cell line, the coding sequence of ORF 57 was amplified using PCR using the following primers: 5'-d CGC GGT ACC CAC ATG TCT ATA ATC GAC TGG GTT (SEQ ID NO:11), 5'-d CGG GGT ACC CTG AGT CAT TAG TAG TAG CTC ATG (SEQ ID NO:12). This PCR fragment was ligated to a TA cloning vector pCRII and designated pAW207.

ORF 16/Apoptosis Suppressor

Due to a lack of convenient restriction sites the coding region wag amplified using PCR, incorporating a PstI site in the 5' coding region, to allow subsequent cloning, using the following primers; 5'-d GCC GAA TCC CAC AGT GCG AAG CTT GCC AGT T (SEQ ID NO:13), 5'-d CGC CTG CAG GGT GTA TAA CTG AGT GTT ACA GC (SEQ ID NO:14), 5'-d GGG CTG CAG GCT GTA CAC TCA GTT ATA CAC C (SEQ ID NO:15), 5' d -CCC GCA TGC ACT TGA TCC AGG ACA TGC TTC (SEQ ID NO:16). This PCR product was ligated with pUC18 to derive pAW208. This plasmid was linearised using PstI and ligated with the lacZ gene under the control of an IE CMV promoter, to generate pAW2-09. A helper cell was constructed using pAW208.

REFERENCES

1 Ledley, F. D. (1994) Non-viral gene therapy *Curr. Opinion Biotech* 5, 626–636.

2 Wagner, E., Cotten, M., Foisner, R., and Birnsteil, M., (1991) Transferrin-polycation complexes: the effect of polycations on the structure of the complex and DNA delivery to cells. *Proc. Natl. Acad. Sci. USA* 88:4255–4259.

3 Rich, D. P., Couture, L. A., Cardoza, L. M. Guiggio, V. M., Armentano, D., Espino, P. C., Hehir, K., Welsh, M. J., Smith, A. E. and Gregory, R. J. (1993) Development and analysis of recombinant adenoviruses for gene therapy of cystic fibrosis. *Hum. Gene Ther.* 4:461–476.

4 Gordon, E. M. and Anderson, W. F. (1994) Gene therapy using retroviral vectors. *Curr. Opinion Biotech.* 5:611–616.

5 Crystal, R. G., McElvaney, N. G., Rosenfeld, M, A., Chu, C., Mastrangeli, A., Hay, J. G., Brody, S. L., Jaffe, H. A., Eissa, N. T. and Danel, C. (1994) Administration of an adenovirus containing the human CFTR cDNA to the respiratory tract of individuals with cystic fibrosis *Nature Genet.* 8:42–51.

6 Locker, H. and Frenkel, N. (1979) Structure and origin of defective genomes contained in serially passaged herpes simplex virus type 1 (Justin). *J Virol.* 29:1065–1077.

7 Davison, A. J. (1993) Herpesvirus genes. *Rev. Med. Virol* 3:237–24

8 Albrecht, J-C., Nicholas, J., Biller, D., Cameron, K. R., Biesinger, B., Newman, C., Wittmann, S., Craxton, M. A,, Coleman, H., Fleckestein, B. and Honess, R. W. (1992) Primary structure of the Herpesvirus saimiri genome. *J Virol.* 66:5047–5048.

9 Jung, J. U., Stager, M., and Desrosiers, R. C. (1994) Virus-encoded cyclin *Mol. Cell Biol.* 14:7235–7244.

10 Biesinger, B., Muller-Fleckenstein, I., Simmers B., Lang, G., Wittmann, S., Platzer, E., Desrosiers, R. C. and Fleckenstein, B (1992) Stable growth transformation of human T lymphocytes by herpesvirus saimiri. *Proc, Natl. Acad. Sci. USA* 89:3116–3119.

11 Murthy, S. C. S., Trimble, J. J, and Desrosiers, R. C. (1989) Deletion mutants of herpesvirus saimiri define an open reading frame necessary for transformation. *J. Virol* 63:3307–3314.

12 Grassmann, R., Fleckenstein B. and Desrosiers, R. C. (1994) Viral transformation of human T lymphocytes. *Adv. Cancer Res.* 63:211–244.

13 Desroisers, R. C., Burghoff, R. L. Bakker, A. and Kamine, J. (1984) Construction of replication-competent herpesvirus saimiri deletion mutants *J. Virol* 49:343–348.

14 Simmer, B., Alt, M., Buckreus, I., Berthold, S., Fleckenstein, B., Platzer, E. and Grassmann, R. (1991) Persistence of selectable herpesvirus saimiri in various human haemopoietic and epithelial cell lines. *J Gen. Virol.* 72:1953–1958.

15 Chang, Y., Cesarman, E., Pessin, M. S., Lee, F., Culpepper, J., Knowles, D. M. and Moore, P. S. (1994) Identification of herpesvirus-like DNA sequences in AIDS-associated Kaposi's sarcoma. *Science* 266:1865–1871.

16 Grassmann, R. and Fleckenstein, B. (1989) Selectable recombinant herpesvirus saimiri is capable of persisting in a human T-cell line. *J. Virol* 63:1818–1821.

17. Berkner, K. L. (1988) Development of Adenovirus vectors for the expression of heterologous genes. *BioTechniques,* 6, 616–629.

18. Glorioso, J., Goins, W. F., and Fink, D. J. (1992) Herpes simplex virus-based vectors *Semin. Virol.* 3:265–276.

19. Gardella, T., Medveczky, P., Sairenji, T. and Mulder, C. (1984) Detection of circular and linear herpesvirus DNA molecules in mammalian cells by gel electrophoresis. *J. Virol.* 50: 248–254.

What is claimed is:

1. An isolated herpesvirus saimiri having at least one mutation in at least one of genes ORF 50 and ORF 57 and wherein the at least one mutation prevents viral replication in a human cell.

2. An isolated herpesvirus saimiri according to claim 1 wherein the virus has a further mutation in a gene so that the virus is unable to transform a target cell and is unable to produce an oncogenic phenotype.

3. An isolated herpesvirus saimiri according to claim 1 wherein the virus has a further mutation in the STP gene.

4. An isolated herpesvirus saimiri according to claim 1 wherein the virus is additionally mutated in at least one gene selected from the group consisting of ORF 4, ORF 14, ORF 15, ORF 16 and ORF 51.

5. An isolated herpesvirus saimiri according to claim 1 wherein the at least one mutation is a complete or partial deletion of the at least one gene.

6. An isolated herpesvirus saimiri according to claim 1 wherein the virus comprises a restriction enzyme insertion site for the insertion of heterologous genetic material.

7. An isolated herpesvirus saimiri according to claim 6 wherein said restriction enzyme insertion site is located in at least one non-coding repeat sequence at the junction between a unique coding region and a non-coding sequence.

8. An isolated herpesvirus saimiri according to claim 5 wherein a restriction enzyme insertion site is present at the deletion site.

9. An isolated herpesvirus saimiri according to claim 6 wherein a restriction enzyme insertion site is provided in at least one gene selected from a group comprising ORF 4, ORF 14, ORF 15, ORF 16 or ORF 51.

10. An isolated herpesvirus saimiri having at least one mutation in at least one of genes ORF 4, ORF 14, ORF 15, ORF 16 and ORF 51.

11. An isolated herpesvirus saimiri according to claim 10 wherein the at least one mutation is a complete or partial deletion of the at least one gene.

12. An isolated herpesvirus saimiri according to claims 10 wherein the virus has a further mutation in a gene so that the virus is unable to transform a target cell and is unable to produce an oncogenic phenotype.

13. An isolated herpesvirus saimiri according to claims 10 wherein said virus has a further mutation in the STP gene.

14. An isolated herpesvirus saimiri according to claim 10 wherein at least part of one of the genes encoding ORF 50 and ORF 57 is mutated or deleted.

15. An isolated herpesvirus saimiri according to claims 10 wherein the virus is provided with a restriction enzyme insertion site in to which heterologous DNA can be inserted.

16. An isolated herpesvirus saimiri having at least one mutation in at least one of genes ORF 4, ORF 14, ORF 15, ORF 16 and ORF 51 and additionally having therein at least one pre-selected heterologous DNA fragment in a deletion site, which site represents a site for partial or whole deletion of at least one gene encoding a non-essential protein and which virus is additionally mutated or deleted for a gene encoding ORF 50 or ORF 57.

17. An isolated herpesvirus saimiri according to claim 16 wherein the virus has a further mutation in a gene so that the virus is unable to transform a target cell and is unable to produce an oncogenic phenotype.

18. An isolated herpesvirus saimiri according to claim 16 wherein the virus has a further mutation in the STP gene.

19. An isolated herpesvirus saimiri having therein at least one pre-selected heterologous DNA fragment in the junction of a single coding region and a non-coding region; and further wherein the virus comprises a reduced number of repetitive non-coding sequences at one or both ends of the single coding region; and the virus also comprises at least one mutation in at least one gene encoding ORF 50 or ORF 57.

20. An isolated herpesvirus saimiri according to claim 19 wherein the copy number of said non-coding repetitive sequence is 5 or less.

21. An isolated herpesvirus saimiri according to claim 19 wherein the copy number of said non-coding repetitive sequence is 1.

22. An isolated herpesvirus saimiri having at least one mutation in one of genes ORF 50 and ORF 51 wherein said mutation prevents viral replication in a human cell and a mutation in a gene encoding a non-essential protein.

23. An isolated herpesvirus saimiri according to claim 22 wherein the virus has a further mutation in a gene so that the virus is unable to transform a target cell and is unable to produce an oncogenic phenotype.

24. An isolated herpesvirus saimiri according to claim 22 wherein the virus has a further mutation in the STP gene.

25. An isolated herpesvirus saimiri according to claim 22 wherein said mutation is a partial or complete deletion of gene ORF 50 or ORF 57.

26. A method for delivering selected heterologous DNA to a target cell by infecting said cell with a recombinant herpesvirus saimiri virus having both at least one mutation in at least one of genes ORF 50 and ORF 57 and a pre-selected heterologous DNA.

27. A method for delivering selected heterologous DNA to a target cell by infecting said cell with a recombinant herpesvirus saimiri virus having both at least one mutation in at least one of genes ORF 4, ORF 14, ORF 15, ORF 16 and ORF 51 and a pre-selected heterologous DNA.

28. A transfected cell transfected with the virus of claim 1.

29. A transfected cell transfected with the virus of claim 10.

30. A transfected cell transfected with the virus of claim 16.

31. A transfected cell transfected with the virus of claim 19.

32. A transfected cell transfected with the virus of claim 22.

* * * * *